US010032003B2

(12) United States Patent
Tong et al.

(10) Patent No.: US 10,032,003 B2
(45) Date of Patent: Jul. 24, 2018

(54) PATIENT MEDICAL DATA ACCESS SYSTEM

(71) Applicant: SIERRA NEVADA CORPORATION, Sparks, NV (US)

(72) Inventors: Kitty Tong, Sparks, NV (US); Richard J. Moss, Sparks, NV (US); Ashkan Moghaddam, Sparks, NV (US); James Rowe, Sparks, NV (US); Joseph T. Sanford, Sparks, NV (US); Brian K. Streng, Sparks, NV (US); Roger Andersen, Sparks, NV (US); David M. Howard, Sparks, NV (US); David C. Uhrig, Sparks, NV (US); Samuel Hancock, Sparks, NV (US); Russell B. Pillers, Sparks, NV (US)

(73) Assignee: SIERRA NEVADA CORPORATION, Sparks, NV (US)

( * ) Notice: Subject to any disclaimer, the term of this patent is extended or adjusted under 35 U.S.C. 154(b) by 198 days.

(21) Appl. No.: 14/166,272

(22) Filed: Jan. 28, 2014

(65) Prior Publication Data
US 2014/0330582 A1 Nov. 6, 2014

Related U.S. Application Data

(60) Provisional application No. 61/819,500, filed on May 3, 2013.

(51) Int. Cl.
G06Q 50/00 (2012.01)
A61B 5/00 (2006.01)
G06F 19/00 (2018.01)

(52) U.S. Cl.
CPC .............................. G06F 19/3418 (2013.01)

(58) Field of Classification Search
CPC ...... G06Q 50/22; G06Q 50/24; A61B 5/0022; A61B 2560/045; G06F 19/3418
(Continued)

(56) References Cited

U.S. PATENT DOCUMENTS 6,072,795 A 6/2000 Poulter
6,363,416 B1 3/2002 Naeimi et al.
(Continued)

OTHER PUBLICATIONS

Comstock, Jonah. "American Well sues Teladoc for alleged patent infringement." Mobilehealthnews.com. Jun. 8, 2015. Web. Retrieved Jun. 29, 2015. Source URL: http://mobihealthnews.com/44163/american-well-sues-teladoc-for-alleged-patent-infringement/.
(Continued)

Primary Examiner — Joy Chng
(74) Attorney, Agent, or Firm — Mintz Levin Cohn Ferris Glovsky and Popeo, P.C.

(57) ABSTRACT

A medical data point of care device is configured to collect, access, store, and distribute patient medical data. The device is particularly suited for use in a mobile environment and may be particularly useful in an urgent care mobile environment, such as a battlefield or disaster area. In such environments, data transmission services may be intermittent and the bandwidth of such services may be low. The device is configured to adjust the flow of data transmission from a point of care location to a remote location so as to maximize or otherwise increase the likelihood of successful transmission of the data. The device is further configured to collect data from both a care provider and a medical device.

16 Claims, 4 Drawing Sheets

(58) Field of Classification Search
USPC .......................................................... 705/2–3
See application file for complete search history.

(56) References Cited

U.S. PATENT DOCUMENTS

| | | |
|---|---|---|
| 6,638,218 B2 | 10/2003 | Bulat |
| 6,757,898 B1 | 6/2004 | Ilsen et al. |
| 6,801,943 B1 | 10/2004 | Pavan et al. |
| 6,839,541 B2 | 1/2005 | Alzoubi et al. |
| 6,889,338 B2 | 5/2005 | Srinivasan et al. |
| 6,993,587 B1 | 1/2006 | Basani et al. |
| 7,011,629 B2 | 3/2006 | Bulat |
| 7,264,590 B2 | 9/2007 | Casey et al. |
| 7,387,607 B2 | 6/2008 | Holt et al. |
| 7,421,578 B1 | 9/2008 | Huang et al. |
| 7,430,608 B2 | 9/2008 | Noonan et al. |
| 7,451,221 B2 | 11/2008 | Basani et al. |
| 7,532,585 B2 | 5/2009 | Kim et al. |
| 7,587,465 B1 | 9/2009 | Muchow |
| 7,590,550 B2 | 9/2009 | Schoenberg |
| 7,649,872 B2 | 1/2010 | Naghian et al. |
| 7,691,059 B2 | 4/2010 | Bulat |
| 7,970,633 B2 | 6/2011 | Bulat |
| 7,974,924 B2 | 7/2011 | Holla et al. |
| 8,126,728 B2 | 2/2012 | Dicks et al. |
| 8,126,729 B2 | 2/2012 | Dicks et al. |
| 8,126,730 B2 | 2/2012 | Dicks et al. |
| 8,131,564 B2 | 3/2012 | Dicks et al. |
| 8,131,565 B2 | 3/2012 | Dicks et al. |
| 8,131,566 B2 | 3/2012 | Dicks et al. |
| 8,140,356 B2 | 3/2012 | Dicks et al. |
| 8,155,982 B2 | 4/2012 | Dicks et al. |
| 8,214,489 B2 | 7/2012 | Ballette et al. |
| 8,225,015 B2 | 7/2012 | Gao-Saari et al. |
| 8,255,238 B2 | 8/2012 | Powell et al. |
| 8,260,709 B2 | 9/2012 | Holla et al. |
| 8,310,336 B2 | 11/2012 | Muhsin et al. |
| 8,380,631 B2 | 2/2013 | Dala et al. |
| 8,396,801 B1 | 3/2013 | Dala et al. |
| 8,396,802 B2 | 3/2013 | Dala et al. |
| 8,396,803 B1 | 3/2013 | Dala et al. |
| 8,396,804 B1 | 3/2013 | Dala et al. |
| 8,549,142 B2 | 10/2013 | Goose et al. |
| 8,583,958 B2 | 11/2013 | Surkov |
| 8,792,384 B2 | 7/2014 | Banerjee et al. |
| 8,908,537 B2 | 12/2014 | Fedyk et al. |
| 8,942,228 B1 | 1/2015 | Chen et al. |
| 9,031,070 B2 | 5/2015 | Mentze et al. |
| 2006/0125356 A1 | 6/2006 | Meek et al. |
| 2007/0152837 A1* | 7/2007 | Bischoff ............. G06F 19/3418 340/573.1 |
| 2007/0213600 A1 | 9/2007 | John et al. |
| 2008/0052127 A1 | 2/2008 | Rosenfeld et al. |
| 2008/0065416 A1 | 3/2008 | Mazar et al. |
| 2008/0088437 A1 | 4/2008 | Aninye et al. |
| 2009/0088607 A1* | 4/2009 | Muraca ................ A61B 5/0002 600/300 |
| 2009/0292555 A1 | 11/2009 | Brown |
| 2010/0318699 A1 | 12/2010 | Gao-Saari et al. |
| 2012/0173281 A1 | 7/2012 | DiLella et al. |
| 2013/0218588 A1 | 8/2013 | Kehr et al. |
| 2014/0330584 A1 | 11/2014 | Pillers et al. |

OTHER PUBLICATIONS

Agrawal, Amar. "Distributed Algorithms for Mobile Ad Hoc Networks." PowerPoint Presentation. Date last modified Apr. 19, 2005. 20 pages.

Al Shayeji, Mohammad, et. al. "Analysis and Enhancements of Leader Elections Algorithms in Mobile Ad Hoc Networks." *ACEEE International Journal of Network Security* vol. 2, No. 4, (2011), 5 pages.

Chandra, Ranveer, et. al. "Anonymous Gossip: Improving Multicast Reliability in Mobile Ad-Hoc Networks." *21st International Conference on Distributed Computing Systems*, (2001), Mesa, AZ. pp. 275-283. 9 pages.

Chung, Hyun, et. al. "Optimal Regional Consecutive Leader Election in Mobile Ad-Hoc Networks." *2011 Proceedings of the 7th ACM SIGACT/SIGMOBILE International Workshop on Foundations of Mobile Computing*, New York, NY. (2011), pp. 52-61. 17 pages.

Jayapal, Cynthia and Sumathi Vembu. "Adaptive Service Discovery Protocol for Mobile Ad Hoc Networks." *European Journal of Scientific Research*, vol. 49, No. 1, (2011), pp. 6-17.

Malpani, Navneet, et. al. "Leader Election Algorithms for Mobile Ad Hoc Networks." *2000 Proceedings of the 4th International Workshop on Discrete Algorithms and Methods for Mobile Computing and Communications*. (2000), pp. 96-103. 8 pages.

Melit, Leila and Nadjib Badache. "A Highly Adaptive Leader Election Algorithm for Mobile Ad Hoc Networks." *International Conference on Advanced Aspects of Software Engineering ICAASE*, Nov. 2-4, 2014, Constantine, Algeria. (2014), pp. 181-184.

Singh, Anu, et. al. "A Process Calculus for Mobile Ad Hoc Networks." *Science of Computer Programming*, vol. 75 No. 6, (2010), pp. 440-469. 19 pages.

Toner, Stephen and Donal O'Mahony. "Self-Organising Node Address Management in Ad-hoc Networks." *Personal Wireless Communications*,(2003), Lecture Notes in Computer Science, vol. 2775. , pp. 476-483. 6 pages.

Vasudevan, Sudarshan, et. al. "Design and Analysis of a Leader Election Algorithm for Mobile Ad Hoc Networks." *2004 Proceedings of the 12th IEEE International Conference on Network Protocols*, Washington, DC. (2004), pp. 350-360. 11 pages.

Vasudevan, Sudarshan, et. al. "Secure Leader Election in Wireless Ad Hoc Networks" Umass Computer Science Technical Report 01-50, (2001). 31 pages.

* cited by examiner

PATIENT MEDICAL DATA ACCESS SYSTEM

REFERENCE TO PRIORITY DOCUMENT

This application claims the benefit of priority under 35 U.S.C. § 119(e) of U.S. Provisional Patent Application Ser. No. 61/819,500 entitled "PATIENT MEDICAL DATA ACCESS SYSTEM" and filed May 3, 2013 under 37 C.F.R. § 1.78(a). Priority of the filing date is hereby claimed and the full disclosure of the aforementioned patent application is incorporated herein by reference.

BACKGROUND

This disclosure relates systems and methods for storing, accessing, and/or distributing patient medical data.

Conventional medical evacuation ("medevac") systems often function in isolation as such systems typically lack any integrated architecture for electronic capture or access of patient information during transit of the patient. Current medevac systems also lack a communication architecture that permits transmission of patient status. As a result, there is a decreased ability to collect and distribute patient information.

Given the lack of access to patient data during transport situations, transport care personnel are typically on their own with respect to managing critically wounded patients during transit of the patient. Survival and recovery rates of patients can be directly attributed to the quality of care provided by transport care personnel with such care being largely dependent on the entire medical transport/care system's access to the patient's relevant medical data. Access to such medical data can be even more important in extreme situations, such as critical traumatic injuries related to accidents or the battlefield, natural disasters, acts of terrorism, etc.

SUMMARY

In view of the foregoing, there is a need for improved systems and methods for collecting, storing, accessing, and/or distributing patient medical data particularly during transport of a patient.

Disclosed are systems and methods that permit medical transport care personnel to rapidly acquire medical data in an autonomous manner, electronically store the data and distribute the data amongst the transport and care systems. The data transmission and access system enables quick and accurate hand-off of patients and efficient preparation of care on arrival at medical facilities. Transport care personnel and medical facility staff can concurrently access a patient's vital statistics, current status and treatments applied, allowing them to collaborate via voice, video, text and data transmissions and thereby provide the patient with quality treatment at the point of injury and while en route to a medical facility.

The disclosed system also permits the monitoring of one or more patients during transport of the patients from one medical facility to another. The disclosed system may also be used at a residence such as to gather data for an in-home monitoring application for the sick and elderly.

In one aspect, there is disclosed a device for transmitting medical data from a point of care location to a remote location, comprising: a housing sized and shaped to be carried by a user; a communication component configured to: (a) identify two or more data elements to be transmitted, wherein the patient data element is a piece of information that is relevant to patient care (in an embodiment, only one data element is identified); (b) assign a priority to each of the patient data elements to be transferred; (c) attempt to transfer the patient data element with the highest priority; (d) cease the attempt to transfer upon passage of a predetermined period of time.

More details of the devices, systems and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or comparatively but are intended to be illustrative. Also, relative placement of features and elements may be modified for the purpose of illustrative clarity.

DETAILED DESCRIPTION

Disclosed is a device that is configured to collect, access, store, and/or distribute patient medical data. The device is particularly suited for use in a mobile environment and may be particularly useful in an urgent care mobile environment, such as a battlefield or disaster area. In such environments, data transmission services may be intermittent and the bandwidth of such services may be low. The device is configured to adjust the flow of data transmission from a point of care location to a remote location so as to maximize or otherwise increase the likelihood of successful transmission of the data. In this regard, there is described herein a data throttling method that prioritizes certain data to be transmitted to ensure that high priority data is properly transmitted.

In addition, the device 105 may include multiple data links for transmission of data. The device is configured to manage multiple communication links simultaneously. This increases the likelihood that data is successfully transmitted to the desired destination, as described in more detail below.

Before the present subject matter is further described, it is to be understood that this subject matter described herein is not limited to particular embodiments described and as such may of course vary. It is also to be understood that the terminology used herein is for the purpose of describing a particular embodiment or embodiments only, and is not intended to be limiting. Unless defined otherwise, all technical terms used herein have the same meaning as commonly understood by one skilled in the art to which this subject matter belongs.

Figure 1:
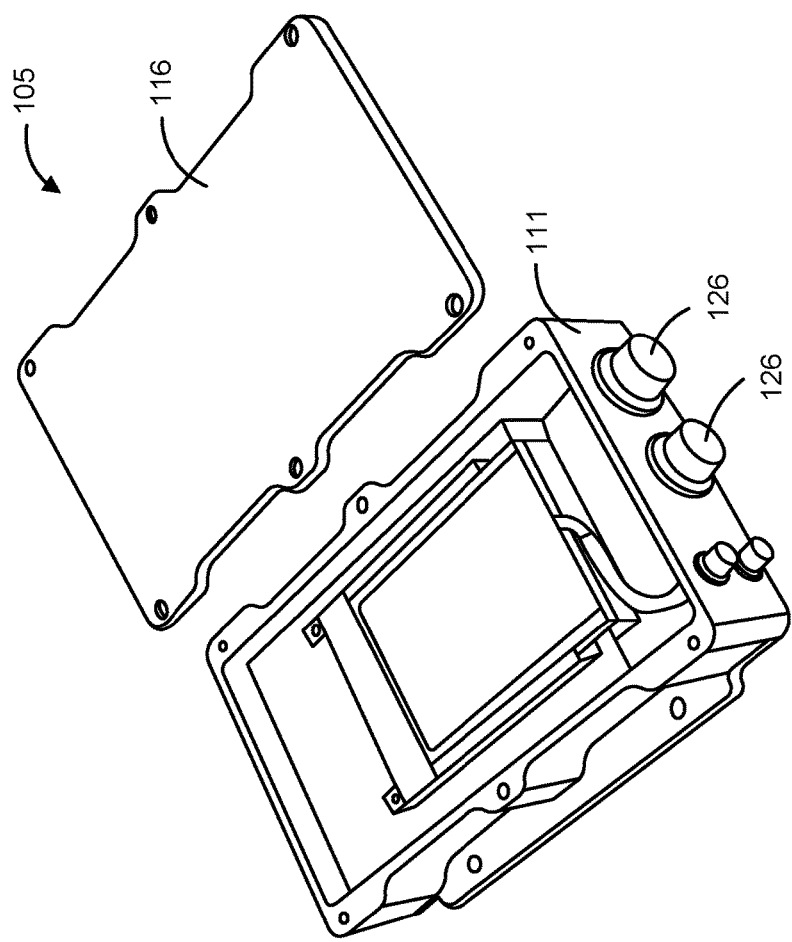
FIG. 1 shows an exemplary embodiment of a device configured to collect, access, store, and/or distribute patient medical data.

FIG. 1 shows an exemplary embodiment of the device 105, which is formed of a housing 110 that can be manufactured of any of a variety of materials, including metal, plastic, composite material, etc. The housing 111 defines an internal cavity that may be exposed by removing a cover 116 that may be secured to the housing 111 in any of a variety of manners, such as by screws, rivets, adhesive, etc. The cavity contains one or more components including electronic and communication components, as described in detail below. The housing 111 includes one or more ports 126 that may be connected to other devices, such as medical devices, communication devices, computers, etc. The device may include an internal power supply or it may be attached to an external power supply.

The housing is sized and shaped so that it may be mounted within or on an emergency medical vehicle, such as a ground ambulance, helicopter, airplane, ship, etc. The housing may be sized such that it can be worn or carried by a person. In this regard, the device 105 may weigh on the order of about 2.4 lbs. and has dimensions of about 2.75"×4"×8". In an embodiment, the device weighs in the range of 2-4 lbs. However, it should be appreciated that the size and shape of the device 105 may vary.

In an alternate embodiment, the device 105 is fixedly or removably mounted in a building such as a house, apartment, nursing home, hospice, or other such habitable place. The device 105 may be connected or coupled to one or more patient medical devices, a connected communication device such as a line of sight, satellite or other type of radio, a power source, and/or a computer controlled device used by patient care personnel. The device may be used to transmit a patient's medical status to a remote monitoring service that can alert a caregiver whenever a medical need arises. This alert may be transmitted through the device via voice, video, text or data communications. In this embodiment, the device is used for long-term monitoring of a patient rather than in an acute emergency situation.

Figure 2:
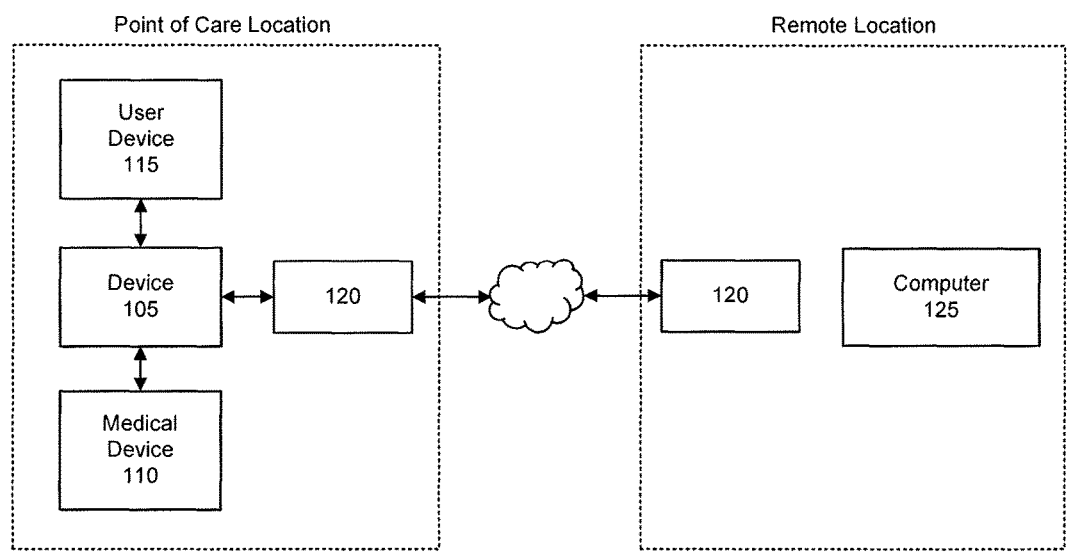
FIG. 2 shows an exemplary communication architecture for use with the device.

FIG. 2 schematically shows an exemplary, high-level operational environment in which the device 105 may be used. The device 105 may be used at a point of care location, which can be any location where a care provider is providing medical care to a patient. In an embodiment, the point of care location is an emergency location such as a vehicle crash, battlefield or disaster site. As mentioned, such environments may have limited communication capabilities that may adversely affect the ability to transmit data. The device 105 may be mounted to a vehicle or may be carried by a person in the point of care location. At the point of care location, the device 105 is communicatively and/or mechanically coupled to at least one medical device 110 (described below) that provides data to the device 105 as described more fully below.

With reference still to FIG. 2, the device 105 is also communicatively coupled to a user device 115, which can be any type of device that the care provider uses to enter, record, store, view and/or maintain data related to the care of the patient. The user device 115 may be, for example, a laptop computer, mobile phone, tablet, data pad, etc. The user device 115 generally includes a data input element such as a keypad and/or touch screen. In an embodiment, the device 105 includes voice recognition software that permits the user to verbally enter data into the device 105. In an embodiment, the user device 115 is held, controlled and/or operated by one or more transport personnel, such as a medic in an emergency environment. The user can input data into the user device 115. The device 105 is configured to receive data from the user device 115, wherein the data may relate to aspects of the patient, such as height, weight, blood pressure, or any data related to the patient. The device 105 is configured to autonomously collect data from the user device and combine the data from the user device 115 with data received from the medical device for transmission. The device 105 communicates with both the medical device and the user device in a plug and play manner. This permits the device 105 to autonomously collect data from the user device and collect data from the medical device without requiring the user to perform any special actions or reconfigure the device 105. It makes for an efficient collection, storage, and/or transmission of the combined data.

A communication component 120 is also coupled to the device 105. The communication component 120 can be any device that is configured to transmit data to a remote location via a communication link, such as a line of sight, satellite or any other type of wireless communication link to the remote location. The communication link may include the Internet, public switched telephone network (PSTN), a private network, etc.

The communication component 120 may include any of a variety of communication devices that are configured to transmit data. For example, the communication component 120 may include one or more antennas, modems, amplifiers, radios, or other types of transceivers, etc. The communication component 120 enables the device 105 to transmit data from a database via wireless transmission (e.g., radio) to an external network in accordance with configured specifications, with the end user being another party such as a medical facility.

Advantageously, the device 105 is configured to monitor and adjust available communication protocols and use an appropriate protocol for efficient transfer of data. The device 105 is configured to interrogate each connected communication component 120 and determine the appropriate communication protocol to use for that radio in a "plug and play" manner, as described more fully below. Transport care personnel can communicate via voice, video, text or data to remotely located care support staff using the device.

With reference still to FIG. 2, the remote location may be any location that is remote from the point of care location. In an example, the remote location is at least more than several miles away from the point of care location. The remote location may be staffed by or accessible by a medical practitioner that can gain access to data transmitted from the device 105. In this regard, the data may be accessed using a computer 125 that resides at the remote location. Or, the data may be accessed using a computer that is remote from the remote location such as via one or more servers coupled to a computer network such as the Internet.

With reference still to FIG. 2, the medical device(s) 110 can include any of a variety of types of medical devices. Such medical device(s) 110 may be connected to the device 105 either via a physical or wireless connection. The connected medical device(s) 110 may include, for example, any number and combination of devices such as: EKG monitor, blood pressure monitor, heart rate monitor, ventilator, defibrillator, IV pump, EEG device, oxygen sensor, cardiovascular reserve index monitor or other similar devices. The device 105 communicates with the medical device 105 and analyzes existing communications links using the most efficient link, or combination of links, to move patient medical information and throttles the data volume transmitted to make the best use of available bandwidth over a communication link, as described in more detail below.

In an embodiment, the device 105 is configured on power-up and/or during operation to receive real-time data from connected medical devices via one or more communication ports 125 (FIG. 1). The device 105 is configured to interrogate each connected medical device 110 (described below) and determine the appropriate communication protocol to use for that device in a "plug and play" manner. A microprocessor inside the device 105 processes the data from the various medical devices and forwards the data to the user device (e.g., a laptop, mobile phone, data pad, etc.)

if necessary. The device 105 also receives configuration and real-time data from the user device. The device 105 may include a microprocessor configured to store all received data into a database in accordance with configuration specifications.

Figure 3:
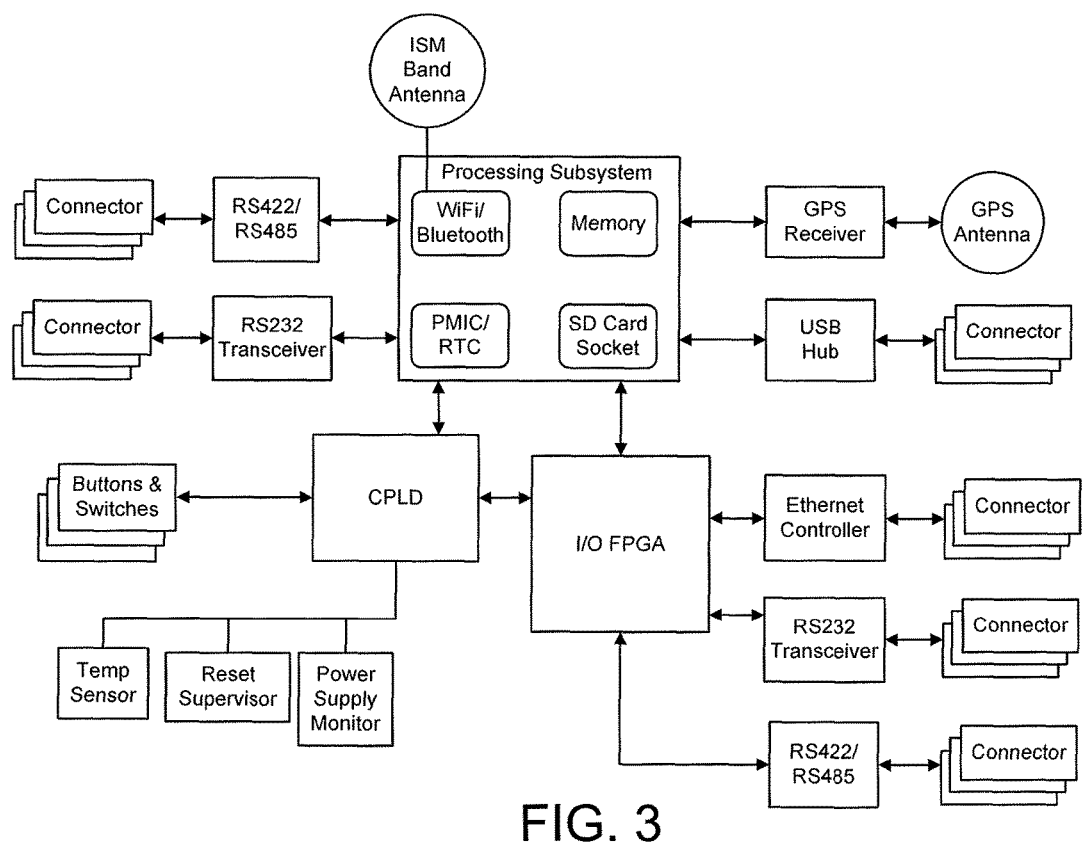
FIG. 3 shows a schematic representation of the device and exemplary components of the device.

FIG. 3 is a schematic representation of the device 105 showing some exemplary components of the device 105. The device may include any of a variety of electronic components, such as one or more printed circuit boards with an embedded microprocessor with internal and/or external memory, and a router with multiple electronic input/output (I/O) connection ports. The I/O ports may include, but are not limited to, any number and combination of interfaces of type such as: Ethernet, RS232, RS422, RS485, USB, MIL-STD-1553, ARINC-429, or other similar interfaces. The device may also include built-in audio and video encoders, radios (802.11 Wi-Fi, Bluetooth, etc.), Global Position System (GPS) receiver, and memory ports for external, removable memory storage such as Secure Digital (SD), Compact Flash, or other similar format types of computer memory storage. The device 105 may include any of a variety of antennas, including a GPS antenna and/or an industrial, scientific and medical band (ISM) antenna, for example. Other types of antennas may be used.

Data Throttling

As mentioned, the device 105 is configured to adjust the flow of data from the Point of Care Location to the Remote Location so as to maximize or otherwise increase the likelihood of successful transmission of the data. This is done by attempting to match sent data volume to available communication bandwidth. In this regard, the device 105 may store or may have access to software that is configured to cause the device 105 to perform one or more operations for adjusting the flow of data.

The device 105 stores the patient data in a data structure wherein the patient data is organized into one or more patient data elements. Each patient data element is associated with a 'priority' wherein the priority indicates a relative value or importance of the patient data element. The priority may vary and may be associated with a situational awareness focused on providing the best care possible.

The priority value may range from a value associated with a highest (or most important priority) to a value associated with a lowest (or least important) priority. For example, the priority may range from one (1) for a "high" to five (5) for a "low" with intermediate values 2, 3, and 4 ranging between the two. This is just an example and it should be appreciated that the range of priority values may vary.

A patient data element may be any piece of information that is relevant to patient care and/or treatment. For example, a patient data element may relate to or indicate patient's blood pressure reading or any other data associated with the patient or the patient's environment. Other examples include the patient's weight, height, age, body temperature, location of the patient, etc.

In the example of the patient's blood pressure, the patient's blood pressure may be assigned, for example, a priority of one (1) while details about the environment or location may be given a lower priority. The actual patient data elements and the corresponding priority value may be assigned in a variety of manners. An expert in the care of critical patients may define a default set of priorities while a care provider or other entity at the point of care location may be able to edit the priority value of each patient data element. Each patient data element may also have an associated timestamp indicating when that piece of information was captured.

The device's transmission of data at the point of care location may operate pursuant to a predetermined method. An exemplary method of transmitting data pursuant to a data-throttling scheme is now described. In a first step, a data transmission cycle begins by starting a timer. The timer defines an amount of time that is allocated for transmitting a patient data element. The value of the timer may vary. It may have a default value or a user may program the value of the timer at the point of care location.

In a next step, the device 105 attempts to transmit any unsent patient data elements, with precedence going to the patient data element with the highest priority value. That is, the unsent patient data element with the highest priority is the one that the device 105 attempts to send first. If the timer expires prior to all of the highest priority data elements being sent, then the method either terminates or the timer is restarted. The device 105 continues to attempt to send the highest priority data elements as long as the timer is not expired. Once the patient data elements with the highest priority are successfully transmitted, and time remains in the cycle, transmission of the next lower priority data begins. When the timer expires, the method returns to the initial step wherein the timer is restarted and the device 105 attempts to send the patient data element with the highest priority. This process continues until the device has successfully transmitted all patient data elements.

Other factors may be taken into account, such as the time stamp of the patient data element. This may ensure that the data being sent to the remote location contains the most recent, most valuable information regarding the patient's condition and care. Specifically, during an individual time cycle of transmission, the data elements of a particular type, e.g. blood pressure, could be sent in order of those with the most recent time stamp first, then proceeding to older entries. The time length of the cycles will be adjustable to allow for fine-tuning.

Multi-Link Management

As mentioned, the device 105 is configured to operate and manage multiple communication links simultaneously. This increases the likelihood that data is successfully transmitted to the desired destination.

Figure 4:
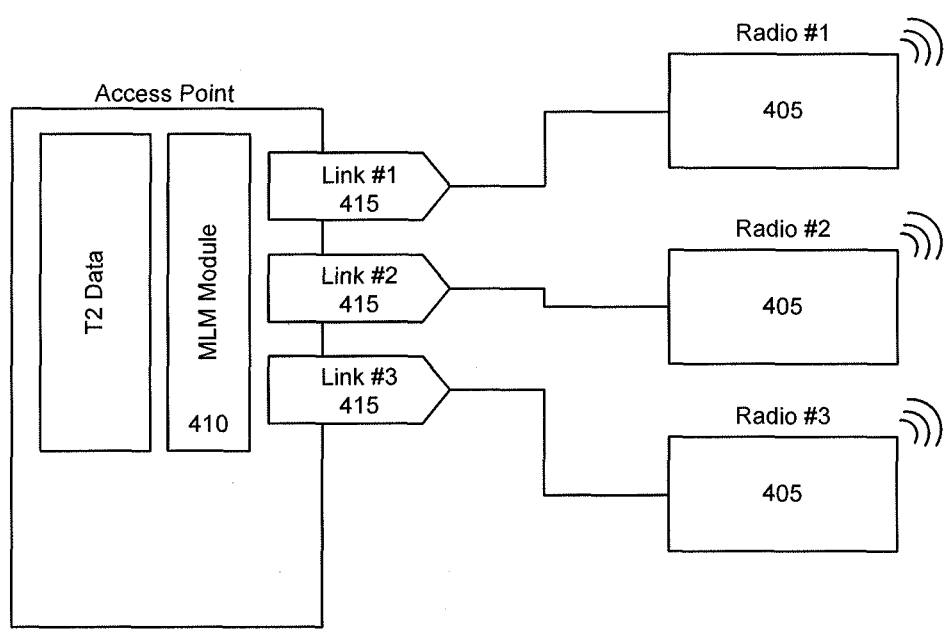
FIG. 4 shows a schematic representation of an exemplary radio configuration of the device.

FIG. 4 shows a schematic representation of an exemplary radio configuration of the device 105, wherein the configuration includes one or more wireless data transmitters, such as radios 405, each configured to wirelessly transmit data. In some embodiments, the links may be of a hardwired type. The radios are connected to or are incorporated into the device 105. The device 105 includes a multi-link management software module (the MLM Module 410) that is programmed to manage multiple data links 415 that are coupled to the radios 405.

The MLM Module 410 is configured to perform and manage several functions. For example, the MLM Module 410 is configured to adapt to changing radio configurations without affecting any high-level local data movement process of the device 105. This may include real-time addition or removal of an active radio 405 from the system. The MLM module 410 also handles identification, management and automatic loading of the individual radio drivers for the device.

The MLM Module 410 attempts to use each link 415 to establish a connection to a ground station, such as a ground station at the point of care location or at a remote location. Once any link is established to a ground station, the module 'handshakes' with that ground station to determine if the ground station is a 'Non-Isolated' ground station or 'Isolated' ground station. An "isolated" ground station does not have a connection to the remote location while an isolated ground station does have a connection. In addition, the MLM Module periodically or continuously evaluates the quality of each radio link to determine its Quality of Service at any given moment. This evaluation includes the entire path to the ground station and, if possible, to the remote location. Then, based on one or more evaluation factors, the MLM determines which link, or links, to use and what type of data to send. The evaluation factors may vary. In an embodiment, the evaluation factors include, for example, link quality, link history, link isolation status, link cost and multiplexing Setting of a local T2 system The multiplexing setting determines if the T2 system is going to multiplex ("bond") multiple links into a single, higher bandwidth link. If the system is set to multiplex, the system sends different data over different links to the same final location. Each multiplexed link used in that case is desirably a non-Isolated link. If the multiplex is turned off, the system uses the best link available to send data. The MLM Module also coordinates the change in mode between sending updates only (Non-Isolated Mode) and full-record (Isolated mode).

Therefore, depending on the bandwidth and amount of each priority data that has not been sent, each transmission cycle will make it so far down into the 'pool' of patient data (highest priority at top, lowest at bottom) that has not yet been sent before starting over.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a device having a display device, such as for example a liquid crystal display (LCD) monitor for displaying information to the user and a keyboard and a input device, such as for example a mouse or a trackball, by which the user may provide input to the device. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

The invention claimed is:

1. A system comprising:
a plurality of medical devices configured to at least generate patient medical data, each medical device having a medical device connection port;
a data input terminal configured to at least facilitate entry of observed patient data by a user of the data input terminal;
a housing having at least one connection port, wherein the connection port of the housing physically and communicatively connects to a connection port of any of the medical devices of the plurality of medical devices;
a communication module, contained within the housing, configured to at least transmit the patient medical data, the communication module comprising:
a plurality of transmitters-configured to wirelessly transmit data over a plurality of communication links to at least one remote server;
at least one processor contained within the housing and communicatively coupled to the at least one connection port and;
at least one memory storing computer readable instructions which, when executed by the processor, cause the processor to perform one or more operations, the one or more operations comprising:
autonomously interrogating, by the at least one processor, each medical device of the plurality of medical devices that is connected to the at least one connection port of the housing;
selecting, by the at least one processor, a first communication protocol for communicating with a first medical device of the plurality of medical devices and a second communication protocol for communicating with a second medical device of the plurality of medical devices, the second communication protocol different from the first communication protocol, the selecting being based on the interrogating of each medical device;

receiving, by the at least one processor, first patient medical data from the first medical device pursuant to the first communication protocol and second patient medical data from the second medical device pursuant to the second communication protocol;

assigning, by the at least one processor, a first priority value to the first patient medical data and a second priority value to the second patient medical data, the first priority value and the second priority value being relevant to patient care;

receiving, from the data input terminal, observed patient data, and autonomously combining the observed patient data with at least the first patient medical data;

assigning, by the at least one processor, a third priority value to the observed patient data, the third priority value being relevant to patient care;

generating, by the at least one processor, a patient medical data object having a plurality of patient data elements having a plurality of priority values, the plurality of patient data elements comprising the first patient medical data having the first priority value, the second patient medical data having the second priority value and the observed patient data having the third priority value, the plurality of patient data elements being arranged based on the plurality of priority values;

storing, by the at least one processor, the patient medical data object in the at least one memory;

interrogating, by the at least one processor, each communication link;

determining, based on the interrogating, a quality of service for each communication link of the plurality of communication links;

selecting, based on the determined quality of service and the plurality of priority values associated with the plurality of patient data elements, a first communication link for transmitting a first patient data element of the plurality of patient data elements; and transmitting, using the first communication link, the first patient data element to the at least one remote server.

2. A system as in claim 1, further comprising starting a timer that runs for predetermined period of time.

3. A system as in claim 1, wherein the communication module further autonomously collects the observed patient data from the data input terminal and combines the autonomously collected observed patient data with the patient medical data from the plurality of medical devices.

4. A system as in claim 1, wherein the plurality of medical devices includes at least one of a EKG monitor, blood pressure monitor, heart rate monitor, ventilator, defibrillator, IV pump, EEG device, oxygen sensor or cardiovascular reserve index monitor.

5. A system as in claim 1, wherein the communication module further comprises an inlet port.

6. A system as in claim 5, wherein the inlet port connects to the data input terminal.

7. A system as in claim 6, wherein the data input terminal is a computer.

8. A system as in claim 1, wherein each of the plurality of communication links is a radio communication link.

9. A system as in claim 8, wherein the radio communication link is supported by a radio transmitter disposed internal to the communication module.

10. A system as in claim 8, wherein the radio communication link is supported by a radio transmitter disposed external to the communication module.

11. A system as in claim 1, wherein the at least one remote server is located at least several miles from the device.

12. A system as in claim 1, wherein the communication module is sized to be carried by a user.

13. A system as in claim 1, wherein the device is sized to fit in a vehicle or in a building.

14. A system as in claim 1, wherein the device connects to the data input terminal or the plurality of medical devices via a wired or wireless connection.

15. A system as in claim 1, wherein the housing is sized and shaped to be mounted within an emergency medical vehicle.

16. A system as in claim 1, wherein the housing weighs in the range of 2 to 4 pounds.

* * * * *